United States Patent [19]

Gerken et al.

[11] Patent Number: 4,663,490

[45] Date of Patent: May 5, 1987

[54] PROCESS FOR THE PRODUCTION OF DINITROTOLUENE

[75] Inventors: Rudolf Gerken; Günter Lailach, both of Krefeld; Dieter Becher, Dormagen; Harro Witt, Kuden, all of Fed. Rep. of Germany

[73] Assignee: Bayer Aktiengesellschaft, Leverkusen, Fed. Rep. of Germany

[21] Appl. No.: 710,895

[22] Filed: Mar. 12, 1985

[30] Foreign Application Priority Data

Mar. 16, 1984 [DE] Fed. Rep. of Germany ....... 3409719

[51] Int. Cl.$^4$ ............................................... C07C 79/10
[52] U.S. Cl. ..................................... 568/934; 568/939
[58] Field of Search ................. 568/934, 939; 260/688

[56] References Cited

U.S. PATENT DOCUMENTS

| | | | |
|---|---|---|---|
| 2,256,999 | 9/1941 | Castner | 568/937 |
| 3,178,481 | 4/1965 | Hauze | 568/934 |
| 4,091,042 | 5/1978 | Alexanderson et al. | 568/939 |
| 4,274,910 | 6/1981 | Forter et al. | 203/86 |
| 4,367,347 | 1/1983 | Sawicki | 568/934 |
| 4,496,782 | 1/1985 | Carr | 568/939 |
| 4,600,702 | 7/1986 | Schumacher | 568/939 |

FOREIGN PATENT DOCUMENTS 1149722 7/1983 Canada .
1152285 8/1983 Canada .
1156428 11/1983 Canada .

Primary Examiner—Edward A. Miller
Attorney, Agent, or Firm—Sprung, Horn, Kramer & Woods

[57] ABSTRACT

In the production of dinitrotoluene by a two-stage reaction of toluene with nitric acid in the presence of sulphuric acid, wherein toluene is nitrated to mononitrotoluene in the first stage using spent acid from the second stage, and the mononitrotoluene is nitrated to dinitrotoluene in the second stage using concentrated spent acid from the first stage, the improvement which comprises concentrating spent acid under vacuum in an indirectly-heated evaporator and feeding mononitrotoluene into the superheated vapor of the evaporator.

13 Claims, 1 Drawing Figure

PROCESS FOR THE PRODUCTION OF DINITROTOLUENE

BACKGROUND OF THE INVENTION

1. Field of the Invention

This invention relates to a process for the production of dinitrotoluene by a two-stage reaction of toluene with nitric acid in the presence of sulphuric acid, toluene being nitrated to mononitrotoluene in the first stage, using the spent acid from the second stage in which the mononitrotoluene is nitrated to dinitrotoluene, using the spent acid from the first stage concentrated under vacuum.

2. Background Information

The removal or recovery of spent sulphuric acid from the production of dinitrotoluene is a problem in that sulphuric acid constitutes a substantial proportion of the production costs. This has in the past led to attempts to obviate the use of sulphuric acid altogether (Kirk-Othmer, Encycl. Chem. Techn. 3rd Edition, 1981, Volume 15, pages 928-929) and to attempts to make the sulphuric acid usable, by more or less elaborate processes for purification, in the fertilizer industry or render it suitable for recirculation before concentration by evaporation (U.S. Pat. No. 4,257,986).

The most widely used process for concentrating spent sulphuric acid by evaporation is the Pauling process (Bodenbrenner, von Plessen, Vollmüller, Dechema-Monogr. 86 (1980), 197), in which a relatively pure 96% sulphuric acid may be recovered.

The disadvantages of this process reside in the high capital investment and operating costs, as well as the formation of $SO_2$ and $NO_x$ compounds and gases due to oxidative decomposition of some of the organic compounds.

Substantial removal or recovery of the organic compounds from spent acid containing sulphuric acid may be achieved according to U.S. Pat. No. 3,856,673 by stripping with steam at temperatures of from 130° to 230° C.

The known methods of concentration of sulphiric acid by evaporation under vacuum (Winnacker. Küchler, Chem. Technol., Vol.2, Anorg. Technol. I, 4th Edition, 1982, pages 70-72) give rise to numerous problems when used for the concentration by evaporation of untreated spent sulphuric acid (hereinafter referred to as "spent" acid) from the production of dinitrotoluene, which has hitherto prevented the use thereof for this purpose. When the toluene nitration process is carried out under optimum conditions, the spent acids contain mainly nitrosyl sulphuric acid, dinitrotoluenes (DNT), mononitrotoluenes (MNT) and nitric acid in addition to water and metal sulphates.

DNT and MNT are volatile in steam and are to a large extent removed by evaporation together with the water. At the low condensation temperatures required for operation under vacuum, DNT crystallizes and causes blockages in the condensation system. The direct condensation of vapors in injection condensers using fresh cooling water is not an economic process because it gives rise to excessive quantities of contaminated waste water and the MNT and DNT contained in the waste acid are lost. If, on the other hand, an indirectly-cooled circulation of vapor condensate is maintained, the solid DNT gives rise to problems similar to those found in vapor condensation on cooled heat exchange surfaces.

It has proved almost impossible to overcome these problems. Removal of the organic constituents by extraction before concentration of the acid by evaporation leads to completely unsatisfactory results. Although the expensive method of steam stripping removes most of the organic compounds, considerable quantities, in particular of 2,4-dinitrotoluene, are left in the spent acid.

SUMMARY OF THE INVENTION

It is an object of the present invention to carry out the recirculation of the spent sulphuric acid from the production of nitrotoluenes by a new process which economically and ecologically is an improvement on the known processes. It is a further object of the present invention to return by far the greater part of the organic compounds to the nitration process and hence render the production of dinitrotoluenes (DNT) even more economical.

It has now suprisingly been found that these aforesaid problems may be overcome by injecting MNT into the super-heated vapors before they enter the indirectly-cooled vapor condenser. According to the present invention, removal of the organic compounds prior to concentration of the spent acid by evaporation is obviated, so that the MNT injected into the vapors may be relatively heavily contaminated with toluene or DNT.

The present invention thus relates to a process for the production of dinitrotoluene by a two-stage reaction of toluene with nitric acid in the presence of sulphuric acid, toluene being nitrated to mononitrotoluene in the first stage using the spent acid from the second stage in which the mononitrotoluene is nitrated to dinitrotoluene using concentrated spent acid from the first stage, characterized in that the spent acid is concentrated by evaporation under vacuum in indirectly-heated evaporators and mononitrotoluene is introduced into the super-heated vapors of the evaporator.

It is particularly advantageous to add the mononitrotoluene in the form of mixtures containing mononitrotoluene, preferably as part of the organic phase which is separated after mononitration of the toluene.

The mononitrotoluene may also be added directly to the waste acid, but injection into the super-heated vapors is preferred for reasons of energy balance. Water or preferably part of the aqueous phase of the vapor condensate is advantageously injected into the vapors at the same time so that the vapors enter the condenser as saturated steam. This enables the cooling surfaces to be kept relatively small.

The spent acid obtained generally has an $H_2SO_4$ concentration of from 65 to 83% and in addition contains mainly toluene, MNT DNT and $NO_x$.

BRIEF DESCRIPTION OF THE DRAWING

The FIGURE is a schematic flow diagram of a process according to the present invention.

DETAILED DESCRIPTION OF THE INVENTION

Figure 1:
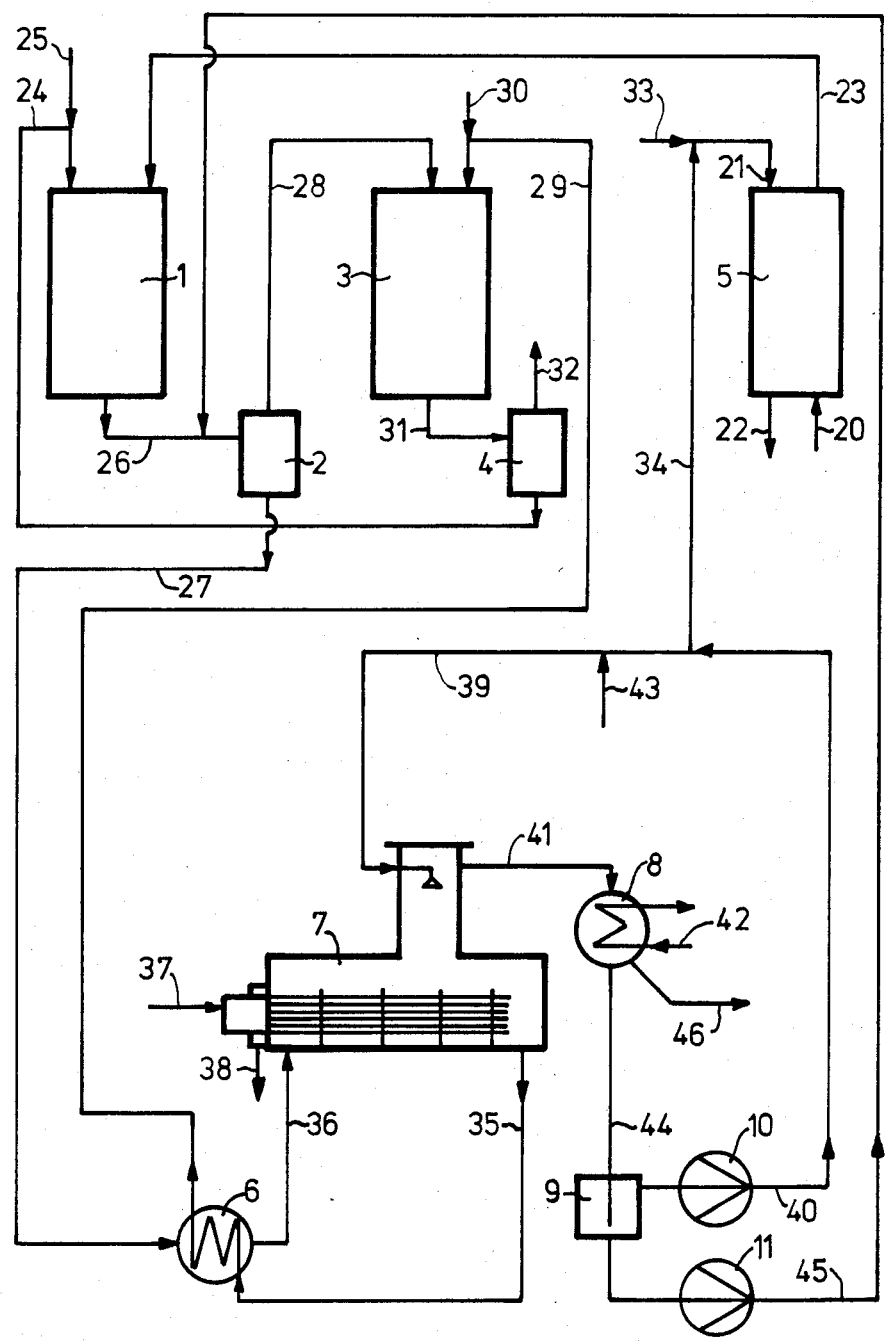

In one particularly preferred embodiment of the process according to the present invention, the spent acid is concentrated by evaporation to a sulphuric acid content of from 88 to 94% $H_2SO_4$ and used for the production of dinitrotoluene and subsequently for the production of mononitrotoluene.

Concentration of the spent acid by evaporation is carried out according to the present invention in horizontal, falling film or circulation evaporators.

In contrast to Pauling vessels which are fired with natural gas or fuel oil, the preferred evaporation process may be carried out using steam as energy carrier. A total reduction in energy consumption to about 60% of that required for the Pauling process may be achieved by the heat exchange between the spent acid fed in and the concentrated acid fed out.

It is advantageous to sub-divide the evaporation process into several stages, each of which may be carried out under optimum conditions. Horizontal evaporators are therefore advantageous for concentrations of up to 94% $H_2SO_4$. The aqueous phase of the condensate of vapor contains only very small quantities of sulphuric acid.

Further saving in energy may be achieved by optimizing the product streams. Thus, it is particularly advantageous to use part of the spent acid separated after production of the dinitrotoluene for the production of mononitrotoluene and then to concentrate it together with the remainder of the spent acid from the production of dinitrotoluene to a sulphuric acid content of from 88 to 94%.

In another embodiment of the process according to the present invention, the from 88 to 94% sulphuric acid is used together with from 98 to 100% $HNO_3$ for the production of dinitrotoluene and subsequently together with from 63 to 70% $HNO_3$ for the production of mononitrotoluene.

The acids which have been concentrated by evaporation according to the present invention may finally be subjected to a process of high-concentration. This may be carried out in circulation evaporators or by the Pauling or the BAYER-Bertrams process (DE-OS No. 3,018,665).

One embodiment of the process according to the present invention therefore involves concentrating the spent acid to a sulphuric acid content of from 88 to 94% by evaporation under vacuum and then to a concentration of from 94 to 97% $H_2SO_4$ by evaporation in a high-concentration stage before it is used again for the production of dinitrotoluene.

According to the present invention, all of the organic phase obtained from the evaporation of waste acid is returned to the nitration process with the result that the DNT yield is significantly increased. The linking of sulphuric acid concentration by evaporation with production of DNT is thus a significant advantage of the present invention.

For removal of $NO_x$, the waste acid may be treated with $SO_2$, sulphuric acid, urea or ammonium sulphate before it is concentrated by evaporation. On the other hand, it may be steam stripped, in which case the nitrogen oxides is absorbed in sodium hydroxide solution with the formation of sodium nitrite after condensation of the steam and steam-volatile compounds. Alternatively, the nitrogen oxides may be destroyed in a reducing flame.

A preferred embodiment of the process according to the present invention is described in detail below with reference to the accompanying drawing which is a flow sheet of the instant process. The figures for concentrations are exemplary and do not restrict the present invention to corresponding values. On the contrary, the present invention is applicable within a wider frame.

The production of dinitrotoluene (DNT) using remake sulphuric acid with a content of from 88 to 94% sulphuric acid and 99% nitric acid and the evaporation of the spent acid having a concentration of from 70 to 82% to a sulphuric acid concentration of from 88 to 94% in a horizontal evaporator is described below.

Toluene (20) is fed into the extraction column (5) in which MNT and DNT are extracted from the waste water (21). The toluene (23) containing MNT and DNT leaving column (5) is fed into the apparatus for mononitration (1). At the same time, the spent acid (24) which has a sulphuric acid content of from 80 to 86% and which has been separated from DNT in separator (4) is fed into the mononitration apparatus (1) together with nitric acid (25). The mixture (26) removed from the mononitration apparatus is separated in separator (2). The from 70 to 82% spent acid (27) flows to the apparatus for acid concentration. The organic phase (28), consisting predominantly of MNT, is fed into the dinitration apparatus (3) together with from 88 to 94% sulphuric acid (29) from the acid evaporation apparatus and fresh approximately 99% nitric acid (30). The mixture (31) removed from the dinitration apparatus (3) is separated in the separator (4). The spent acid (24) enters the mononitration apparatus (1).

The crude DNT (32) is washed free from acid in the conventional manner. The resulting water (33) containing DNT and MNT is introduced into the extraction column (5) together with the aqueous phase of the vapor condensate (34) from the waste acid evaporator and freed from nitro-compounds by extraction with toluene (20) before it is carried to a waste water treatment as organically-contaminated waste water (22).

The from 70 to 82% spent acid (27) obtained from mononitration apparatus (1), separated from MNT (28) in separator (2), is heated to from 100° to 130° C. (36) in the heat exchanger (6) in counter-current to the sulphuric acid (35) discharged from the horizontal evaporator (7) and is fed into the evaporator (7), optionally by way of a flash evaporator.

The heat exchanger of the horizontal evaporator (7) consists of a bundle of tantalum pipes heated using steam (37) at from 170° to 210° C., preferably from 170° to 195° C. The condensate (38) may advantageously be used for the generation of steam.

Evaporation is carried out under a pressure of from 20 to 150 mbar, preferably from 40 to 100 mbar. The from 88 to 94% sulphuric acid (35) discharged from evaporator (7) at from 170° to 195° C., preferably from 170° to 185° C., is cooled to about 60° C. in heat exchanger (6). Further cooling with water to about 40° C. is advisable before the acid (29) is fed into the dinitration apparatus (3).

The super-heated vapors are cooled to the saturation temperature of the vapor by the injection of water or preferably part (39) of the aqueous phase (40) of the vapor condensate. To prevent solidification of organic compounds in the pipes and the water cooled (42) condensation system (8) used for the vapors, MNT (43), preferably the organic phase (28) from mononitration (1), are fed into the super-heated vapors, separately or together with the aqueous phase. The lower the condensation temperature and the smaller the ratio of MNT to DNT in the vapors, the larger is the quantity of MNT required.

According to the present invention, the ratio of MNT to DNT in the organic phase of the vapor condensate should be not less than 2:1, but in any event less than 10:1. Ratios of from 4:1 to 7:1 are preferred. In practice, MNT or a mixture containing MNT is added in such quantities that deposition of solid dinitrotoluenes in the plant is safely avoided.

The vapor condensate (44) is discharged into a vessel (9) from which the organic phase (45) is discharged by a pump (11) to the nitration apparatus, while the aqueous phase (40) is discharged by the pump (10) to the apparatus for waste water extraction (5). The organic phase of the vapor condensate (45) is preferably fed into the nitration system immediately after mononitration apparatus (1). These parts (46) of the vapors (41) which cannot be condensed are removed by the vacuum pump after vapor condensation. The vacuum pump is preferably a liquid ring pump operated with water or sulphuric acid as sealing liquid, preferably the concentrated sulphuric acid before its return to dinitration apparatus (3).

In another embodiment of the process according to the present invention, a partial stream of the sulphuric acid (24) which in this case has a concentration of from 83 to 86% is directly carried to the heat exchanger (6) and only so much sulphuric acid is transferred to the mononitration apparatus (1) that the sulphuric acid (27) removed from this stage by way of the separator (2) will have a concentration of from 70 to 80% $H_2SO_4$. As the two partial streams are mixed, an $H_2SO_4$ concentration of from about 78 to 82% is again obtained at the entry to the spent acid evaporator (7).

In a preferred embodiment, all the from 83 to 86% spent acid (24) is transferred from dinitration (3) to mononitration (1) and a from 64 to 70% nitric acid is used for mononitration instead of approximately 99% nitric acid (25).

In another embodiment of the process according to the present invention, the from about 90 to 94% sulphuric acid (29) is concentrated to from 94 to 97% $H_2SO_4$ in a high-concentration stage and the highly concentrated acid is used for dinitration (3). To avoid blockage by the small quantities of dinitrotoluene which evaporate in the process of high-concentration, MNT may be injected into the vapor condensation system of high-concentration, optionally periodically.

Other forms of low pressure evaporators may be used in place of the above-described horizontal evaporator for concentration of the spent acid by evaporation to from about 88 to 94% $H_2SO_4$.

In larger plants, it may be advantageous to carry out the evaporation of spent acid to a concentration of from 88 to 94% $H_2SO_4$ in a series of evaporators operated at different low pressures.

If acid circulation is maintained for a considerable period, metal salts entering the sulphuric acid with the nitric acid or by corrosion are liable to crystallize from the concentrated acid on cooling in the heat exchanger (6) and must be removed by periodic rinsing with water or dilute acid.

The advantages of the process according to the present invention will be demonstrated by the following non-limiting examples. Concentration of the spent acid by evaporation was carried out in accordance with the drawing to which reference is made in the examples.

EXAMPLE 1 (COMPARISON EXAMPLE)

The spent acid (27) from mononitration (1) had the following composition:
76.0% $H_2SO_4$
1.5% nitrosyl hydrogen sulphate
0.4% DNT
0.15% MNT
0.03% $HNO_3$.

3.4 t/h of this spent acid were pre-heated to 100° C. in heat exchanger (6), consisting of two tubular glass heat exchangers in series, and fed into the horizontal evaporator (7). The bundle of tantalum pipes of the evaporator was heated to 195° C. with saturated steam (37). The steam consumption was 1.2 t/h. Water was evaporated from the waste acid at a pressure of 45 mbar. 2.777 t/h of concentrated acid (35) were discharged at 182° C. and cooled to 40° C. in the heat exchanger before being fed into the dinitration stage (2). The concentrated acid (35) had the following composition:
92.0% $H_2SO_4$
1.4% nitrosyl hydrogen sulphate
0.007% DNT
MNT and $HNO_3$ could not be detected.

The super-heated vapors (41) were cooled to about 40° C. by the injection of 100 l/h of the aqueous phase of the vapor condensate (40) before they entered the vapor condenser (8), a water-cooled tubular heat exchanger. The vapor condensate (44) flowed into the vessel (9) at a temperature of from 25° to 30° C. The vacuum of 45 mbar was maintained by means of a water ring pump which was used to withdraw gases (46) which could not be condensed and feed them to a sodium hydroxide scrubber for removal of the nitrous gases.

Immediately after the apparatus for spent acid evaporation was put into operation, solid deposits of DNT formed on the walls of the glass pipes conducting vapor from the evaporator (7) to the condenser (8). Evaporation broke down after about 5 hours due to the pipes of the vapor condenser (8) being almost completely blocked by solid DNT in the upper region so that the vacuum in the evaporator could no longer be maintained. The pipes carrying vapor condensate from the condenser (8) to the vessel (9) were also heavily blocked with solid DNT in several places.

EXAMPLE 2

Evaporation was carried out in a manner analogous to Example 1, but 55 kg/h of crude MNT (28) were injected into the super-heated vapors together with the aqueous vapor condensate (40). Deposition of solid DNT in the vapor condensation system was thereby avoided. The organic phase of vapor condensate (44) removed from vessel (9) was liquid. It contained 4.3 times as much MNT as DNT. It was fed into the separator (2) together with the discharge (26) from mononitration (1).

EXAMPLE 3

3 t/h of spent acid (corresponding to Example 1) were concentrated to 89.0% $H_2SO_4$ by evaporation under a pressure of 100 mbar in the horizontal evaporator (7). Water was evaporated at the rate of 422 kg/h. The concentrated acid discharged still contained 0.02% DNT. At temperatures of 45° C. at the inlet to the condenser and 30° C. at the condenser outlet, the addition of 30 kg/h of crude MNT (28) to the waste acid fed in was sufficient to prevent deposition of solid DNT in the vapor condensation system. The MNT:DNT ratio in the organic phase of the vapor condensate (44) was 2.8:1.

It will be appreciated that the instant specification and examples are set froth by way of illustration and not limitation, and that various modifications and changes may be made without departing from the spirit and scope of the present invention.

We claim:

1. In the production of dinitrotoluene by a two-stage reaction of toluene with nitric acid in the presence of sulphuric acid, wherein toluene is nitrated to mononitrotoluene in the first stage using spent acid from the second stage, and the mononitrotoluene is nitrated to dinitrotoluene in the second stage using concentrated spent acid from the first stage, the improvement which comprises concentrating spent acid under vacuum in an indirectly-heated evaporator and feeding mononitrotoluene into the superheated vapor of the evaporator.

2. A process according to claim 1, wherein the mononitrotoluene is fed to the superheated vapor of the evaporator in the form of a mixture containing mononitrotoluene.

3. A process according to claim 1, including the further step of separating the first stage nitration product into an aqueous phase and an organic phase, the organic phase containing mononitrotoluene, and feeding such nitrotoluene into the vapor of the evaporator.

4. A process according to claim 1, wherein the ratio of mononitrotoluene to dinitrotoluene in the organic phase of the condensate of the super-heated vapor of the evaporator is from about 2:1 to 10:1.

5. A process according to claim 1, wherein the ratio of mononitrotoluene to dinitrotoluene in the organic phase of the condensate of the superheated vapor of the evaporator is from about 4:1 to 7:1.

6. A process according to claim 1, wherein water is injected into the super-heated vapor of the evaporator.

7. A process according to claim 6, wherein the water injected is part of the aqueous phase of the vapor condensate from the evaporator.

8. A process according to claim 1, wherein the spent acid from the first stage is concentrated in the first stage to a sulphuric acid content of from 88 to 94% $H_2SO_4$ by evaporation and used for the production of dinitrotoluene and subsequently for the production of mononitrotoluene.

9. A process according to claim 8, wherein concentration of the spent acid by evaporation is carried out in horizontal evaporators.

10. A process according to claim 8, wherein concentration of the spent acid by evaporation is carried out in falling-film or circulation evaporators.

11. A process according to claim 1, wherein part of the spent acid separated after production of the dinitrotoluene is used for the production of mononitrotoluene and is subsequently concentrated to a sulphuric acid content of from 88 to 94% by evaporation.

12. A process according to claim 5, wherein from 88 to 94% sulphuric acid is used in the second stage together with from 98 to 100% $HNO_3$ and the partly diluted acid formed is subsequently used in the first stage together with from 63 to 70% $HNO_3$.

13. A process according to claim 1, wherein the spent acid is concentrated by evaporation to a sulphuric acid content of from 88 to 94% and subsequently concentrated by water evaporation to from 94 to 97% $H_2SO_4$ in a stage of high-concentration before it is used again for the production of dinitrotoluene.

* * * * *